(12) United States Patent
Teeuwen (10) Patent No.: US 11,961,607 B2
(45) Date of Patent: Apr. 16, 2024

(54) DIGITAL IMAGE TRANSFER SYSTEM

(71) Applicant: Jaap Teeuwen, Haarlem (NL)

(72) Inventor: Jaap Teeuwen, Haarlem (NL)

( * ) Notice: Subject to any disclaimer, the term of this patent is extended or adjusted under 35 U.S.C. 154(b) by 780 days.

(21) Appl. No.: 17/063,342

(22) Filed: Oct. 5, 2020

(65) Prior Publication Data

US 2021/0090719 A1 Mar. 25, 2021

Related U.S. Application Data

(63) Continuation of application No. PCT/NL2019/050206, filed on Apr. 5, 2019.

(30) Foreign Application Priority Data

Apr. 5, 2018 (NL) .................................... 2020723

(51) Int. Cl.
| | |
|---|---|
| *G06F 13/00* | (2006.01) |
| *G06T 7/00* | (2017.01) |
| *G16H 30/20* | (2018.01) |
| *G16H 30/40* | (2018.01) |
| *H04L 49/90* | (2022.01) |
| *H04N 1/00* | (2006.01) |

(52) U.S. Cl.
CPC ........... *G16H 30/40* (2018.01); *G06T 7/0012* (2013.01); *G16H 30/20* (2018.01); *H04L 49/90* (2013.01); *H04N 1/00095* (2013.01); *G06T 2207/10081* (2013.01); *G06T 2207/10088* (2013.01); *G06T 2207/10104* (2013.01)

(58) Field of Classification Search
CPC ......... G06T 7/0012; G06T 2207/10081; G06T 2207/10088; G06T 2207/10104; G16H 30/40; G16H 30/20; G16H 40/20; G16H 50/20; G16H 10/60; G16H 15/00; H04L 49/90; H04N 1/00095
USPC .................. 709/213, 223, 203; 382/131, 132
See application file for complete search history.

(56) References Cited

U.S. PATENT DOCUMENTS

| | | | | |
|---|---|---|---|---|
| 9,881,127 | B2 * | 1/2018 | Westin | ................ G06F 16/5866 |
| 9,984,203 | B2 * | 5/2018 | Westin | .................... H04L 67/06 |
| 10,037,406 | B2 * | 7/2018 | Westin | .................. G16H 40/67 |
| 10,387,196 | B2 * | 8/2019 | Rahme | ................ G06F 16/5866 |

(Continued)

FOREIGN PATENT DOCUMENTS

| | | |
|---|---|---|
| WO | 2013/188850 | 12/2013 |
| WO | 2016/086289 | 6/2016 |
| WO | 2019/194678 | 10/2019 |

OTHER PUBLICATIONS

Montoya, J. C., et al., "3D Deep Learning Angiography (3D-DLA) from C-arm Conebeam CT", American Journal of Neuroradiology, vol. 39, No. 5, 2018, 916-922.

(Continued)

*Primary Examiner* — Kenneth R Coulter
(74) *Attorney, Agent, or Firm* — Peacock Law P.C.; Justin R. Muehlmeyer (57) ABSTRACT

Systems and methods for a digital image transfer system for guaranteed high speed and failsafe transfer and deep learning analysis of complicated digital images. In particular, the transfer methods and systems are suited for medical images, such as CT and MR scans, especially when a large number of images needs to be transferred and looked at immediately, such as when a patient is acute danger of life.

13 Claims, 5 Drawing Sheets

(56) References Cited

U.S. PATENT DOCUMENTS

| | | | | |
|---|---|---|---|---|
| 10,665,339 B2* | 5/2020 | Westin | ................... | H04L 67/06 |
| 10,665,340 B2* | 5/2020 | Westin | ................... | G16H 30/20 |
| 10,748,648 B2* | 8/2020 | Westin | ................... | G16H 30/40 |
| 11,206,245 B2* | 12/2021 | Westin | ................... | G16H 30/40 |
| 11,462,314 B2* | 10/2022 | Westin | ................... | H04N 23/64 |
| 11,735,312 B2* | 8/2023 | Westin | ................. | G06F 16/116 |
| | | | | 707/E17.044 |
| 2017/0300358 A1* | 10/2017 | Rahme | ................... | G16H 30/20 |

OTHER PUBLICATIONS

Shams, Ramtin, et al., "A Survey of Medical Image Registration on Multicore and the GPU", IEEE Signal Processing Magazine, vol. 27, No. 2, 2010, 50-60.

Uecker, Martin, et al., "Nonlinear Inverse Reconstruction for Real-Time MRI of the Human Heart Using Undersampled Radial FLASH", Magnetic Resonance in Medicine, vol. 6, 2010, 1456-1462.

* cited by examiner

DIGITAL IMAGE TRANSFER SYSTEM

CROSS-REFERENCE TO RELATED APPLICATIONS

This application is a continuation application of International Patent Application No. PCT/NL2019/050206, entitled "Digital Image Transfer System", filed on Apr. 5, 2019, which claims priority to Netherlands Patent Application No. 2020723, entitled "Digital Image Transfer System", filed on Apr. 5, 2018, and the specification and claims thereof are incorporated herein by reference.

FIELD OF THE INVENTION

Embodiments of the present invention are in the field of digital image transfer systems, and use of said system for guaranteed high speed and failsafe transfer and deep learning analysis of complicated digital images. In particular, embodiments of the present invention are suited for medical images, such as CT and MR scans, especially when a large number of images needs to be transferred and looked at immediately, such as when a patient is acute danger of life.

BACKGROUND OF THE INVENTION

Currently, there is a lack in capability for both fast transfer and analysis of medical images for diagnosis support purposes in time critical situations. Slowness of existing solutions is typically caused by two main factors: 1) technical constraints in current transfer capabilities, despite 4G or 5G network capacity and landline capacity, 2) technical constraints in current analysis capabilities, unable to execute advanced deep learning using complicated image data in compliance with demanding time critical application.

Both transfer of medical images becomes time critical in cases where speed of (initial) treatment is essential for the patient's outcome.

Diagnosis may depend on availability of 1) these medical experts and 2) a medical image for diagnosis (i.e. CT scan of the patient's brain). Both must be available to prevent time loss in time critical situations.

The simple solution is to transfer the images to experts in a different location. However, there is a lack in capability for transfer of medical images fast enough to be useful for diagnosis support purposes in time critical situation.

Existing solutions for image transfer are slow and often subject to error (causing even more slowness).

Furthermore, diagnosis support resulting from artificial intelligence, which may be less used for application in time critical cases. Some reasons are due to constraints of hardware/(hospital) computers are limited in terms of processing speed and scalability, for diagnosis support purposes in time critical situations image analysis cannot be guaranteed to be (consistently) fast enough to be usable. It may (next to speed) also be not performant enough to enable guaranteed failsafe and reliable execution of artificial intelligence, which may be a precondition to apply artificial intelligence for diagnosis support in critical situations (e.g. a patient is in acute danger of life).

Some references relate to image transfer or image processing. Montoya in an article in American J. Neuroradiology, Vol. 39, No. 5, 22 Mar. 2018, p. 916-922 describes deep learning strategies. Shams in IEEE Signal Processing Magazine, Piscataway, N.J., Vol. 27, No. 2, Mar. 1, 2010, p. 50-60 describes multicore processing for medical image registration. WO 2016/086289 A1 is an example of tele-stroke application, comprising machine learning and analysis of imaging data, and WO 2013/188850 A1 recites use of metadata for determining if image data needs to be converted.

As a consequence, a patient may be transferred from one location (hospital) to a hospital located further away. In too many instances such a transfer involves a too long drive and as a consequence the patient has died before arriving at the other hospital.

Embodiments of the present invention relate to a digital image transfer system, which solves one or more of the above problems and drawbacks of the prior art, providing reliable results, without jeopardizing functionality and advantages.

Note that this application refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

SUMMARY OF THE INVENTION

Embodiments of the present invention relate to a system for transfer and analysis of digital images. Reference is made to Dutch priority Patent Application 2020723, which application and its contents are incorporated by reference. Within mind to improve the outcome of stroke patients, a technical solution was designed and built suitable for time critical use, in particular to support medical doctors in diagnosis of stroke. This solution applies deep learning techniques (artificial intelligence) for automated analysis of these images, such as CT scans, which may basically use one or more elements of the sequence of 1. prepare medical images for secure transfer from source; 2. secure transfer of medical images from source to analysis environment; 3. detect, gather and store newly received medical images and their metadata; 4: orchestrated execution of required analysis algorithms (and their interdependence) for: a. setup, scale and control technical environments for all of the required algorithms; b: perform algorithms to establish purpose, priority and destination of image data to achieve maximum speed in diagnosis support, by both "routing" and prioritizing the image processing through system in the appropriate and most efficient way, plus finding the most suitable/best available destination to receive the analysis outcome (both diagnosis support reporting and transferred image data); c. perform analysis algorithms for optimization of both image data and method of transfer of image data to achieve maximum speed of image data transfer; d. deep learning contents (medical) analysis for diagnosis support; 5. optimization (scope, divide/slice, convert, compress and prioritize transfer order) medical images in accordance with analysis results in the most efficient/fastest way possible; 6. transfer optimized image data in calculated priority order/sequence to destination device; 7. Re-arrange the transferred optimized medical images for diagnosis support at any type of destination device for interpretation/examination of the image data by a (medical) expert, typically for diagnosis purposes. Next to viewing, browsing and windowing the medical image and its metadata, human expert interpretation may include providing interpretation data by the system's features including measuring (e.g. blood volumes of haemorrhage), marking (e.g. annotations), forwarding the medical image (e.g. to a different medical expert), replying/answering to the source the image data originated from). Such interpretation data may be returned to the system and stored for further processing. 8. Gather the analysis result for reporting; 9. Send analysis report to recipient (e.g. via direct messaging, or email). The present solution is particularly designed for speed: images are transferred and analysed as fast as possible, typically within 3 minutes from the moment a new (CT) scan is made, until the doctor receives the analysis report, mostly within one minute, and quite often within 30 seconds. Testing the present solution in hospitals pointed out that medical specialists were very enthusiastic about the mere speed of the analysis, even more than the analysis results. The solution is fast, and provides secure and failsafe and reliable transfer of medical images, such as 15-100000 images, in order to comply with demanding time critical requirements. It can be used location independent and on any mobile device. The recipient e.g. medical doctor may receive the image using any display, such as a smart phone, a computer, a pad, etc. The present invention uses a unique design pattern to bypass prior art constraints.

The present system is dedicated for fast, secure, and failsafe transfer and analysis of digital images.

Transfer of image data from any type of source and device, to any type of destination device and from any location to any other location, wherein locations are typically spaced apart, such as spaced >1 km apart, e.g. >10 km spaced apart, is achieved. To achieve maximum speed in transferring the image data, analysis algorithms for deep learning (artificial intelligence) may be used to establish the most efficient technical way of transfer and the most effective way in getting the transferred image data to the right destination (based on aspects including location, skills/specialisms, availability, agreements between parties).

Analysis of image data is particularly designed for secure, fast and failsafe contents/medical analysis of images (next analysis for optimal efficient and effective image data transfer), in essence in a highly controlled and highly scalable machine learning environment applying deep learning algorithms, using ultrafast (and theoretically infinitely scalable) technology, specifically graphical processing units (GPUs), as applied in the initial version of the system as tested in hospitals, and tensor processing units to be used specifically for neural network machine learning.

The system may typically always be up, in order to transfer images at any point in time, typically upon request e.g. when making a brain scan of a stroke patient is detected or expected to be made. A size of images may be 1-500 Mb per image. An image may have 100*100 to 5000*5000 pixels, such as 200*200 to 2500*2500 pixels. An image may have data related to pixel information, e.g. contrast and RGB info, and data related to the image itself, such as patient identification, date, place, etc., which data may be anonymized. As such a user, such as a medical doctor, of said images may be considered not to have direct access to the images. The present system comprises an input for receiving a plurality of digitized images, which may be a wireless or wired input, and combinations thereof.

Images may be transferred from 1. an image generator to the present system or 2. from an administrative filing system to the present system. Transfer from an image generator is typical when diagnosis support is needed as fast as possible, in cases such as stroke, due to the acute and time critical nature of stroke. For less time critical application, image data may be transferred from any administrative source such as PACSs (picture archiving and communication system) in hospitals, per individual image or per batch of images, e.g. for population screenings and for research purposes, including collecting (archived) images to feed and further develop the system's machine learning capabilities.

A dedicated system may comprise at least >10 parallel operable processors, preferably >100 processors, more preferably >1000 processors, such as >$10^4$ processors, e.g. >$10^5$ processors processes and transfers the images. Thereto an image inbox 12 for digital images is present receiving and storing images, such as form a scanning device, typically through the input. An orchestrator 62 is provided for managing tasks of components of the present transfer system. The orchestrator comprises a rule engine 63 which determines rules to be followed, a virtual machine manager 64, such as for managing the multitude of processors, a transceiver controller 65, a queue arranger driver which can drive the queue arranger, an algorithm executor driver which can drive the algorithm executor 66, an input in use receiving images from the message queue arranger 50, an output in use providing images to a reporting servicer 58, and an output in use providing instructions to an algorithm executor 66. In a hierarchal sense the orchestrator 62 is relatively high positioned, above most of the components or parallel therewith. An image files queue is provided for ordering received images, such as in view of images considered most relevant are processed first. For instance, images representing slice of a central part of the brain may be processed first.

The orchestrator 62 may interact with artificial intelligent algorithms in this respect. The 51 image files queue arranger may comprise an input in use receiving images from the image inbox 12, an input in use receiving images from the algorithm executor 66, an output in use providing images to a 58 reporting servicer, and an output in use providing images to the orchestrator 62. Further an Algorithm executor 66 is provided for identifying most relevant parts of images, for pattern recognition, for amending images to highlight certain aspects thereof, etc. The algorithm executor 66 comprises analysis algorithms 67, wherein the algorithms comprise at least two layers in use analysing the image, an input in use receiving images from the message queue arranger 50, an input in use receiving images from an 19 image storage, an input in use receiving instructions from the orchestrator 62, an output in use providing processed images to a 58 reporting servicer, and an output in use providing feedback to the 50 message queue arranger. The present system further comprises a 54 data exchange controller for communicating with the outside world, such as with a user, and for providing instructions to the present system. The data exchange controller comprises an input in use receiving instructions from a user, an output in use providing processed images to a 58 reporting servicer, and an output in use providing processed and unprocessed images to a 58 reporting servicer. Further the 58 reporting servicer is provided, comprising an input in use receiving processed images from the algorithm executor 66, an input in use receiving instructions from the data exchange controller 54, an input in use receiving images from the 50 message queue arranger, and an output in use providing reports to the data exchange controller 54 or user. Also an image storage 19 and a metadata storage 28 may be present. An output for transferring at least one digitized and processed image to a receiving device is also provided.

Use may be made of an Advanced Neurovascular Image Analysis and Quotation system (ANIAQ) particularly designed to solve technical constraints in prior art. The present ANIAQ may be unique in fast, secure, failsafe and compliant transfer and analysis of medical images: within 3 minutes and typically within 10 seconds after a patient's image has been recorded in a (CT) scanner, doctors and specialists can view and browse the images, using any device, anywhere in the world. The present ANIAQ enables built-in, modular artificial intelligence for diagnosis support, e.g. based on analysis of a (CT) scan, ANIAQ may indicate type, location, severity of stroke, indicating the necessity to transfer the CT images to be viewed and judged by a doctor elsewhere.

The present invention relates to a method of fast transfer of digital images. The method operates the present image transfer system and comprises receiving a plurality of images in the 12 image inbox, typically medical scans, such as sliced scans of a brain, arranging the plurality of images by the 50 message queue arranger, processing a first image on instruction of orchestrator 62 by algorithm executor 66, reporting the processed image by the reporter service, and repeating processing and reporting for subsequent images.

Advantages of the present description are detailed throughout the description. Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

SUMMARY OF THE FIGURES

FIGS. 1-5 show certain aspects of the present image transfer system. All figures are described in further detail herein. The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention. In the drawings:

DETAILED DESCRIPTION OF THE INVENTION

In an exemplary embodiment of the present transfer system the data exchange controller 54 may comprise at least one of an access control manager 55, and image API 56, and a metadata API 57.

In an exemplary embodiment of the present transfer system the message queues arranger 50 may comprise at least one of an image files queues arranger 51, an algorithm input queues arranger 52, and an algorithm output queues arranger 53.

In an exemplary embodiment of the present transfer system the reporting servicer 58 may comprise at least one of a direct message reporter 59, and an email reporter 60.

In an exemplary embodiment the present transfer system may comprise a 28 metadata storage, comprising an input in use receiving instructions from the orchestrator 62, an input in use receiving instructions from the data exchange controller 54, and an output in use providing data to the report servicer 58.

In an exemplary embodiment the present transfer system may comprise an image converter 13 receiving the plurality of digitized images for dividing parts of an image and transferring said parts to the respective multitude of processors of the dedicated system.

In an exemplary embodiment the present transfer system may comprise an image re-assembler 74 for reassembling processed parts of the dedicated system.

In an exemplary embodiment of the present transfer system each individual processor may have a response time of <20 sec, (dedicated and prioritising).

In an exemplary embodiment of the present transfer system each individual processor may have an uptime of >99.5%.

In an exemplary embodiment of the present transfer system each individual processor may have an MTBF of >10 days.

In an exemplary embodiment of the present transfer system the image may be selected from a CT scan, an MRI scan, a PET scan and a Mammography scan.

In an exemplary embodiment of the present transfer system the image may be selected from a brain scan.

In an exemplary embodiment of the present transfer system each available processor may be labelled with a success rate chance label.

In an exemplary embodiment of the present transfer system in use sub-image parts may be identified and labelled by the orchestrator 62 and stored in metadata storage 28, based on the results of image contents analysis algorithms 68 and/or technical image analysis algorithms 69 and/or contextual image analysis algorithms 70 and/or synthesis analysis algorithms 71 as executed by the algorithm executor 66.

In an exemplary embodiment the present transfer system may comprise a trigger 99 for starting an information loop.

In an exemplary embodiment the present transfer system may comprise an image slicer 16, the image slicer may be capable of converting 3D-images into high precision 48 bit decimal 2D-sliced images. It is considered that in view of time huge advantages may be obtained thereby, wherein typical transfer-times are reduced from minutes to seconds. For slicing typically deep learning techniques may be used, the deep learning techniques identifying the in view of later medical analysis most important slices. The most important slices may be transferred first and unimportant slices may be excluded from transfer. The slicer may be regarded as content driven, transferring the most relevant images first. In order to be capable of slicing efficiently typically the present high number of processors is required. Fast transfer is especially important in cases of life threatening situations.

In an exemplary embodiment the present transfer system may comprise an image precision compressor 17, wherein the image slicer precision compressor converts a high precision slice, such as a 48 bit decimal slice, into a low precision slice, such as a 16 bit whole number slice. Typically first the low precision (or resolution) slice is transferred, and then typically quickly thereafter the high precision slice is transferred. The low and high precision slices are then integrated.

In an exemplary embodiment the present transfer system may comprise a GZIP compressor 18, wherein the low precision slice and high precision slice may be compressed.

In an exemplary embodiment the present transfer system may comprise an image cache 73 which in used is capable of decompressing images.

In an exemplary embodiment the present transfer system may comprise an image converter 13 capable of converting an image into a byte array format, a 57 metadata API, an 56 image API, the image converter having an input capable of receiving images, and an output capable of transferring converted images to a 57 metadata API and to an 56 image API, the metadata API 57 having an input capable of receiving metadata from the image converter 13 and an output capable of transferring metadata to the re-assembler 74, the image API 56 having an input capable of receiving image data from the image converter 13 and an output capable of transferring image data to a 72 fast image transceiver.

Embodiments of the present invention will hereafter be further elucidated through the following examples which are exemplary and explanatory of nature and are not intended to be considered limiting of the invention. To the person skilled in the art it may be clear that many variants, being obvious or not, may be conceivable falling within the scope of protection, defined by the present claims.

EXAMPLES

The below describes a schematic method of operation, wherein actions indicated may be performed in another order, may be left out, or further actions may be added.

In a first step medical images are captured (e.g. by CT scanning device) or selected/retrieved (e.g. from a hospital's file system). A specification of purpose/goal of image files to be transferred by the present system is given, such as a fast transfer of the images to a recipient/destination, and/or an automated analysis to determine data for diagnosis support, storing the analysis outcome and metadata for diagnosis support reporting and deep learning purposes, and/or any type of reporting, including reporting outcome of automated analysis for diagnosis support to a recipient/destination. Securing transfer of images from a source/sender to the system. Detection, gathering, storage and logging of newly received image files. Determining purpose/goal of newly received images. Determining analysis method for received images. Determining destination(s) and/or recipient(s) of image(s) to be transferred and/or report(s) to be sent. Notifying/alerting (intended) recipient(s)/destination(s) about upcoming urgent message(s) to be received (transferred images and/or diagnosis support report.

Processing image files in accordance with determined purpose, with a fast transfer of the image files.

Performing automated analysis and optimization of the image files, preparing for fast transfer. Providing optimized image files to appropriate destination(s)/recipient(s), in relevance according to analysis results, and/or providing an automated analysis for diagnosis support, with an automated analysis of the image files for diagnosis report, gathering analysis data and set up diagnosis report, and reporting outcome of automated analysis for diagnosis support to a recipient/destination to be specified or determined by automated analysis.

Figure 2:
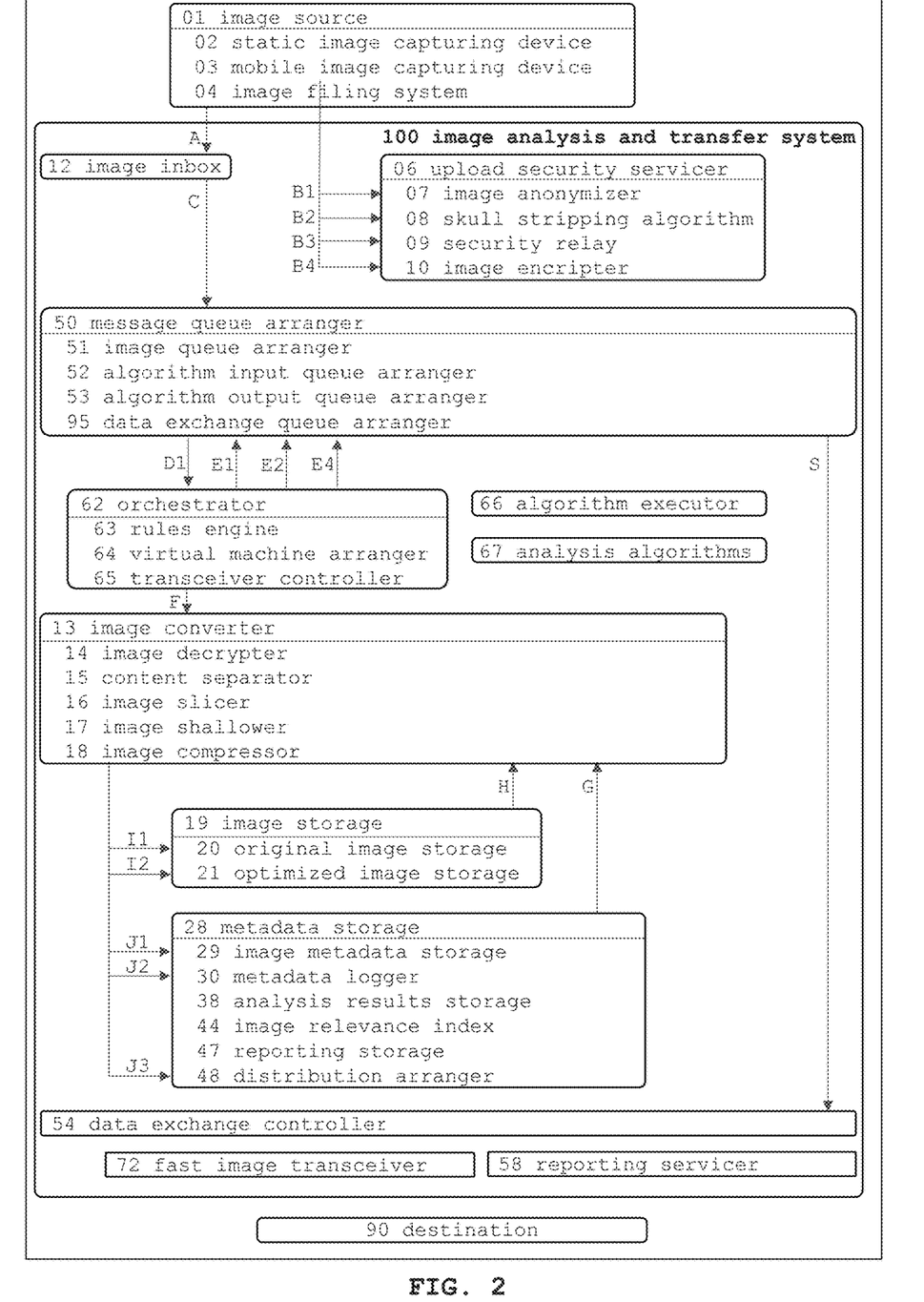
FIG. 2 shows schematics of the present system, depicting a simplified flow of import and storage of an image.

Examples of getting an image into the present system (some details are in FIG. 2 plus accompanying description):

Image files may be uploaded from a facility using an image capturing device (e.g. CT scanning device), which may be static or ambulatory (e.g. mobile scanning device in emergency helicopter or ambulance). Also filing systems may be used as a source to import single or multiple image files (e.g. for population screenings and for research purposes, including collecting (archived) images to feed and further develop the system's machine learning capabilities). Any type of image origin 01, (including static image capturer 02, mobile image capturer 03, image filing system 04 may trigger secure import autonomously. In case additional security measures are required, image file import may use secure upload servicer 06 e.g. to anonymize the image's metadata and its contents, e.g. by erasing or masking privacy sensitive parts of the picture, e.g. since skull structure visible on CT scans of a stroke person's head may be regarded as privacy sensitive data, the present system's skull stripping algorithm 08 (which may also be used as occurrence of image contents analysis algorithms 69 may be used to erase skull structure from the CT scan, leaving just the brains, which may be transferred to the present system unencrypted as brains may be regarded non-privacy sensitive data. Secure upload of an image file may be started automatically as soon as e.g. CT scanning commences or is announced to commence; to trigger image inbox 12 to automatically import the uploaded image file. Inbox 12 may trigger decryption and/or any preparation to increase efficient processing, which may include metadata separator 15 to separate metadata from contents. Such preparation may reduce file size up to 50%, since in formats/protocols a large part of image files may consist of metadata irrelevant for the purpose of file transfer. Such preparation may also include deselection of irrelevant contents, e.g. triggering skull stripping algorithm 08 or similar. Image inbox 12 may trigger message queue arranger 50 to queue the new file for processing; image storage 19 to store contents; metadata storage 28 to store metadata.

Example of image analysis (some details are in FIG. 3 plus accompanying description): in particular for image analysis processing, the present system may depend on its architecture of orchestrated hierarchy to ensure seamless and trustworthy performance for time critical use. In a hierarchal sense the orchestrator 62 is relatively high positioned, above most of the components or parallel therewith. This example shows some aspects how orchestrator 62 is a determining factor in steering both the present system's functional behaviour and non-functional behaviour.

Figure 3:
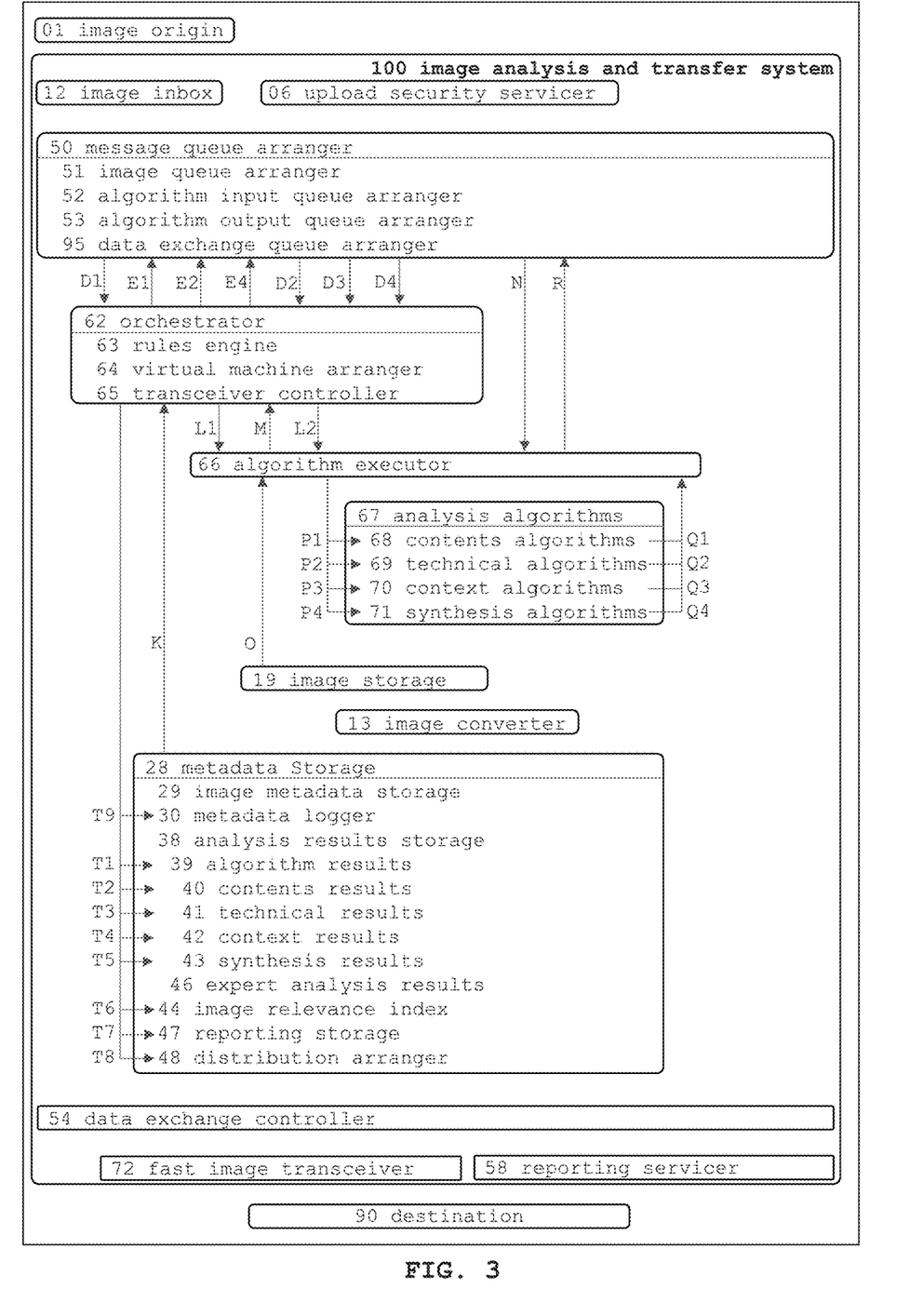
FIG. 3 shows schematics of the present system, depicting a simplified flow of image analysis.

Orchestrator 62 may continuously monitor all aspects relevant to the present system. Orchestrator 62 may collect and store any monitoring data, including events (e.g. an image's analysis is completed) and performance (e.g. of algorithms when in use use). Orchestrator 62 may trigger its rules engine 63 for rule based determination and assignment of actions required for any combination of events. Orchestrator may trigger message queue arranger 50 to accordingly store or alter any type of determined action and their priority in queue. Orchestrator 62 may trigger message queue arranger 50 to alter a queued image's priority, i.e. its order in queue for processing related to other queued images, and to register or alter the analysis method required for a file. This may be done for any file, at any time, including new files, immediately after receipt by inbox 12. Orchestrator 62 may trigger rules engine 63 to evaluate and determine a file's priority and required method of analysis. Method of analysis may include any combination in any hierarchy and order of any types of analysis algorithms 67 and may per type include different occurrences (e.g. analysis may require 4 occurrences of image contents analysis algorithms 68, which may be interdepending, 1 occurrence of technical analysis algorithm 69 which must be run twice for some reason, e.g.

running an occurrence of contextual analysis algorithms 70 provided results causing reconsideration of already provided technical analysis). Orchestrator 62 may trigger message queue arranger 50 to alter a queued files priority and to register assigned analysis algorithms in queue in accordance with order and hierarchy as determined.

Priority in queue may trigger the analysis process, typically starting with virtual machine manager 64 to set up required environment and resources needed by algorithm executor 66. Algorithm executor 66 may execute analysis algorithms 67 in accordance with queue sequences as provided by message arranger 50. Algorithm executor 66 may return any (intermediate) analysis results to message queue arranger 50, triggering registration of algorithms output queues, which may be used as input for subsequent analysis.

Orchestrator 62 may continuously monitor and steer all aspects relevant to the analysis process, including availability and performance of technical environment. After completion of the analysis process for a queued file, rules engine 63 may trigger virtual machine manager 64 to terminate or suspend all sessions/environments/virtual machines.

Orchestrator 62 may trigger metadata storage 28 to store monitoring metadata for different purposes, including compliance, traceability, technical analysis and optimization of the present system's performance.

Next to queues for images and algorithms, message queue arranger 50 may comprise different types of queue (e.g. collaboration in image analysis, e.g. compliance reporting).

Example of storage of analysis result and subsequent image conversion (some details are in FIG. 3 plus accompanying description): rules engine 63 may trigger metadata storage 28 to store metadata, which may include reports, logging metadata and analysis algorithm results of any kind. Analysis outcome may include levels of relevance of parts of images. This may be stored by image relevance index 44, triggering image converter 13 to convert image data and other formats. In conversion, particularly the concept of slicing is considered an important enabler in steering image transfer efficiency. Some reasons may be: slicing may enable viewing 3D image data via generic channels and devices, such as smart phones, tablets and regular (non-specialized) computers; slicing may enable image transfer in a way that is scoped (only the relevant parts), prioritized (most relevant parts to be transferred first) and modular (e.g. image viewing can start as early as the very first slice is transferred, unlike 3D transfers); slicing may benefit from technologies which enable significant efficiency gains (e.g. regarding to scalable processing, caching, compression, rendering).

Image relevance index 44 may comprise metadata identifying which parts of a 3D image's image data is deemed as most relevant, which may be based on analysis algorithms results and/or (medical) experts' judgement and/or applied rules (e.g. by rules engine 63). Basically, image relevance index 44 maps the 3D Image file in a way anticipating for and corresponding with the 2D format, the so called "slices", and the 3D image may need to be converted to by image converter 13. Next to that, image relevance index's 44 map is used as a reference for further processing image slices in correspondence with their relevance, which may be leading is leading throughout all subsequent processes converting, optimizing, transferring, re-arranging and viewing the image.

Image converter 13 may trigger original image storage 20 to retrieve the (originally received) 3D image files; to trigger image slicer (16), converting the 3D image data into 2D Image Data high precision format ("slices") starting with the part of the 3D image data that is deemed as most relevant following the metadata provided by image relevance index 44, then the next part in relevance order, and so on; in accordance with this particular order of relevance; to let image precision compressor 17 convert the high precision 2D image data slices into a low precision (16 bit whole number) format for transfer in the fastest way possible, though with less detail; to trigger GZIP compressor 18 to let each 2D slice (both in low precision 16 bit whole number format and in high precision 48 bit decimal format) being compressed in GZIP format to reduce size and to further enhance transfer in the fastest way possible; to trigger image storage 19 to store each individual resulting slice format. Image converter 13 may continue performing above mentioned sequence of steps until the entire 3D image data has been converted into 2d image slices, in the exact order of relevance and scope (complete image or limited to relevant parts) as established by the analysis algorithms.

Examples of image transfer and viewing (some details are in FIGS. 5A and 5B plus accompanying description): since relevance order in slicing is essential for image transfer, this example starts with some further elaboration of the slicing concept. Image relevance order may be the order in which 2D slices represent the most important part of a 3D image file, typically (in cases of stroke) the part image of the brain showing the stroke. Relevance order is used to scope and prioritize breakdown, transfer, re-arranging and viewing of the image data. Relevance order may vary depending on maturity of machine learning, especially in contents analysis for diagnosis support. Ultimately, the latter may be decisive in judging which part of an image is most relevant and important to be transferred and viewed first. In a simplified example: in case of haemorrhage the contents analysis algorithms will detect which part of the brain, blood volume, diameter etc. The most relevant part of the 3D image file likely will be where the haemorrhage has the largest diameter. The relevance order of the 2D slices in that case typically may be: start with transfer of compressed low precision slices best representing the largest diameter of the haemorrhage, then the slice above it (slice +1), then the slice beneath it (−1, then +2, then 31 2 and so on until this representation of the haemorrhage is transferred sufficiently for viewing the most important part of the 3D image. "Sufficiently" may either be completely (all slices regarding the haemorrhage), or sufficiently as judged by machine learning, based on how haemorrhage is viewed in common practice: e.g. specialists may typically look at the 20% slices representing the "centre", the 5% of each furthest edge as and 5% of the brain tissue surrounding the haemorrhage as identified by the image contents analysis algorithms).

Figure 5A:
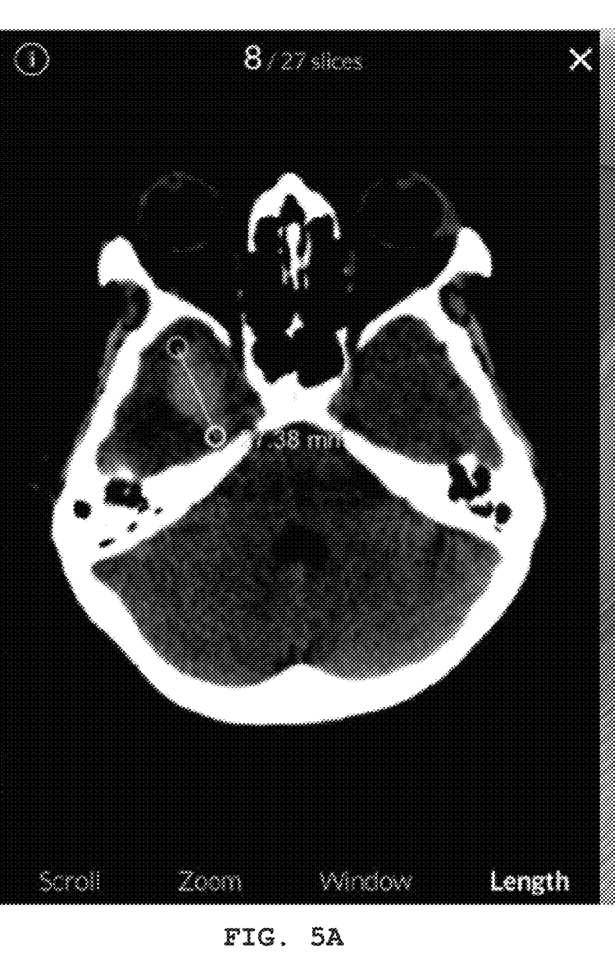
FIGS. 5A and 5B show an image and transferred image.
Figure 5B:
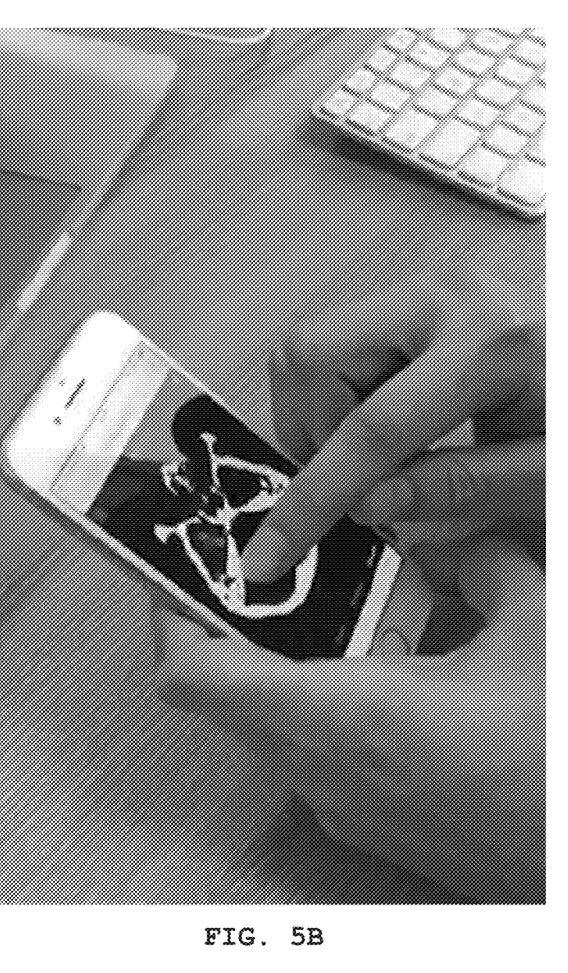

For continuous development in (machine) learning which part of 3D images is most relevant, data of actual viewing by humans may be collected and applied in machine learning, next to and interdependent with image contents analysis algorithms. Subsequently after the most relevant part of the 3D image has been "covered" by 2D low precision slices, 2D high precision slices representing the same most relevant part may be transferred. After that, the next parts in relevance order may be transferred in 2D low precision, subsequently in 2D high precision, and so on, until the least important parts are transferred.

A (simplified) example of applying "common sense" rules may be starting a relevance order with 2D slices where brain has the largest diameter because of statistical likeliness that "something" of interest is to be seen there, rather than 2D slices where brain diameter is smallest, which will have the lowest priority).

A (simplified) example of applying medical statistics rules may be starting a relevance order with 2D slices of the brain part where statistically (in most cases) "something" of interest is to be seen (e.g. about 85% of all strokes are ischaemic and 15% haemorrhagic, highest relevance order then is part of the brain where ischaemic stroke statistically occurs most).

A (simplified) example of applying experience/learning form actual use and viewing images in practice: initially the highest relevance order basically may be the part of the brain which is typically viewed first, assuming that medical experts know where to look first from experience. A step further is assigning highest relevance order to part of the brain which appeared (was likely) to be most relevant in viewing (e.g. viewed most intensively: parts viewed longest, parts where most windowing and browsing was done) and of course, the most precise variant: which parts of the image were actually assigned as most relevant in viewing by registered feedback and measurements from medical staff who viewed and judged the transferred. Note that all variants in assigning relevance based on applying experience/learning form actual use and viewing images in practice, obviously may be related to experience, specialism, working method, etc. of the viewers involved and therefore may differ per individual. In particular here continuous (machine) learning and optimization promises fast and relatively easy progress (e.g. viewing patterns from experts may be applied to help novices where to look first).

Next to the slice order relevance as such, an optimal balance between transfer of high and low precision slices may be an important factor to gain speed in transfer and viewing of image files. This will be further developed in algorithms (particularly in technical image analysis algorithms 69) and in rules to be applied by the orchestrator's 62 rules engine 63, adding the application of factors such as (e.g.) available connection speed (developing countries), resolution and processing speed of devices used etc. and any other circumstantial/environmental relevant matters (typical opening times, lunchtime breaks, siestas) will be introduced to further refine the process to establish the optimal relationship between transfer of high and low precision slices.

Over time, thanks to increasing technical means (transfer speed, processing power of GPUs in mobile devices etc.) one may expect that optimization for speed of transfer and viewing of complicated image data (3D=>2D, high/low precision, relevance order, re-arranging etc.) as claimed in this patent application might become less effective (e.g. that optimization might not be necessary anymore thanks to increased capabilities of technical means).

The opposite may be true: not alone will the concept of optimization as claimed in this patent empower even faster transfer and processing of even more complicated image files when technical constraints demise; above that, the whole pattern of modular, phased and scalable deep learning methods integrally takes into account the increase of technical capabilities—it is one of the major variables in the evolutionary continuous learning as claimed in this patent application. Above is a simplified example, reality may be more complicated e.g. by the fact that CT scans are typically build up in horizontal or vertical layers (slices) while the largest diameter may be diagonal, and/or the haemorrhage is spread/multiple, and/or the haemorrhage exists in combination with (even may by caused by) ischemic stroke.

The example flow of image transfer and viewing: orchestrator 62 may trigger outgoing image transfer at any time rules engine 63 decided to do so, by letting reporting servicer 58 send an alert to a user about an upcoming image transfer, the alert may typically be send by direct message reporter 59 and in some cases by email reporter 60. A user might trigger outgoing image transfer autonomously, e.g. when fast image transceiver 72 is used to view images already available (e.g. a previously made CT scan). A user may trigger data exchange controller 54 to initiate the outgoing image transfer process by letting access control manager 55 check the user's authenticity and authority, if the user is entitled, metadata API 57 may trigger distribution metadata storage 48 to retrieve and provide all relevant metadata regarding the addressed user, destination the image data needs to be transferred to (as established by the analysis algorithms), including any relevant metadata regarding the device (previously and/or usually) used by the destination user; let metadata API 57 retrieve and provide any relevant metadata regarding the actual device currently used by the destination; establish if the (expected) device of destination (device used to receive the image data to be transferred) is able to decompress the GZIP format (some old browsers are unable to do so). Furthermore, metadata API 57 may trigger metadata storage 28 to retrieve and provide all metadata relevant for outgoing image transfer, which may include image relevance index, reports, algorithm analysis results, earlier registered human expert analysis results, including measurements and annotations, which may include hypothesis, remarks, advices, measurements (e.g. blood volume), follow-up actions (e.g. image file forwarding or reply), status, conclusions, etc.

Data exchanger 54 may trigger fast image transceiver 72, by letting Metadata API 57 transfer relevant metadata to fast image transceiver 72, which may include metadata retrieved from image relevance index 44. Data exchanger 54 may trigger image API 56 to transfer 2d slices (which may be in compressed format, e.g. lossless Compressed GZIP 5-gzip data using highly optimized code) to fast image transceiver 72. Image API 56 may transfer 2d slices in accordance with image relevance index until all (relevant) slices have been transferred. Fast image transceiver 72 may trigger the image re-assembler 74 by providing image relevance index, whereas image relevance index may be prescriptive for image re-assembler 74 in which order re-assembling must occur.

Fast image transceiver 72 may receive 2D slices from Image API 56 (any GZIP format may be automatically decompressed by browser); fast image transceiver 72 may provide 2D slices to image cache 73, triggering image re-assembler 74 to compose 3D image simulation by re-arranging 2D slices in accordance with the image relevance index; browser on device may trigger GL Viewer 75, which uses Graphical Processing Unit (GPU) instead of CPU; browser on device may trigger measurement annotation servicer 76 which captures metadata regarding viewing (including browsing, zooming, windowing, measurements and annotations, follow-up such as forward/reply); measurement annotation servicer 76 may trigger metadata API 57 by providing any relevant viewing metadata; metadata API 57 may trigger metadata storage 28 to store all relevant metadata; metadata storage 28 may trigger orchestrator 62 to determine required actions, which may be new actions (e.g. regarding sending a reply message coming from fast image transceiver 72 to the image origin, e.g. forwarding the transferred image to a different user).

Example: Determine Destination(s)/Recipient(s) of Image Transfer and/or Report

Destination(s) and/or recipient(s) may be specified by sender/source of the image file, or by user of fast image transceiver 72. Specified destination(s)/recipients may be fixed or preferred. The present system may automatically determine destination/recipient by performing an analysis to determine destination(s)/recipient(s) based on (dynamic) criteria. This may improve diagnosis speed e.g. by quick determination of a (or any) available expert capable and entitled to analyse a transferred image and/or analysis report. This may be useful as such, or as a back-up e.g. in case a specified recipient cannot be reached in time.

Simple automated determination of destination(s)/recipient(s) initially may be performed by the orchestrator's 62 rules engine 63. Further development includes methods whereas rules engine 63 utilizes and interacts with algorithm executor 66. Rules engine 63 may determine the analysis method. A simple analysis may comprise execution of a single occurrence of analysis algorithms 70. A more advanced analysis method may be to firstly perform contents analysis algorithms 68, taking the contents analysis results in consideration in letting context analysis algorithms 70 find the best matching available expert. E.g. contents analysis results indicate an ischaemic stroke with characteristics demanding a particularly specialized expert. This input may be of help in getting the best and fastest diagnosis and treatment as. Though there might be a long way to go before such is common practice, this is a simple example of what can be achieved.

Communication regarding automated determination of destination/recipient may be performed by fast image transceiver 72 and reporting servicer 58. This may be simple, but effective and may be relatively quickly operational. Data exchanger 54 may be used for this purpose, e.g. in direct communication with hospital IT systems though this might take longer to become operational). Some further details: automated determination of destination/recipient may involve (automated or manual) confirmation of readiness and willingness of any (intended) recipient/destination to accept either decline to receive and process upcoming urgent message(s) according to (case specific or general) constraints, agreements and/or protocols. In case of declining or no (timely) response: keep performing analysis to determine (next best) destination(s)/recipient(s) based on (dynamic) criteria, and requesting confirmation of readiness and willingness of candidate recipient(s)/destination(s), until sufficient destination(s)/recipient(s) confirmed readiness and willingness, or if no sufficient confirmation(s) are received within a (dynamic) timeframe, then perform an analysis to determine destination(s)/recipient(s) based on (dynamic) criteria according to "best effort" scenario (typically a range of possible destinations/recipients, first available/accepting then confirms/accepts).

Example: Reporting

Orchestrator 62 may detect urgency to report, e.g. reporting results to a user after completion of image analysis, triggering message queue arranger 50 to let its reporting queue arranger 95 queue the report. Data exchanger 54v may monitor reporting queue arranger's 95 queue, triggering metadata storage 28 to provide relevant data for reporting and reporting distribution, including triggering distribution arranger 48, report storage 47. Metadata API 57 may trigger reporting servicer 58, providing reporting and distribution metadata; reporting servicer 58 may trigger any of its channels, including, direct message servicer 59 to distribute report, email servicer 60.

Example: Exporting Images

Reporting may generally concern metadata. Images may generally be transferred by fast image transfer using fast image transceiver 72. Also the present system may transfer/export multitudes of images, using a bulk image exporter to send images to a destination and/or using data exchanger 54 to allow controlled user access to retrieve or store any relevant from or to the platform. Image inbox 12 may be used for receiving multitudes of images.

Some further functional details are described in more examples, illustrated by FIGS. 1-4.

DETAILED DESCRIPTION OF FIGURES

Figure 4:
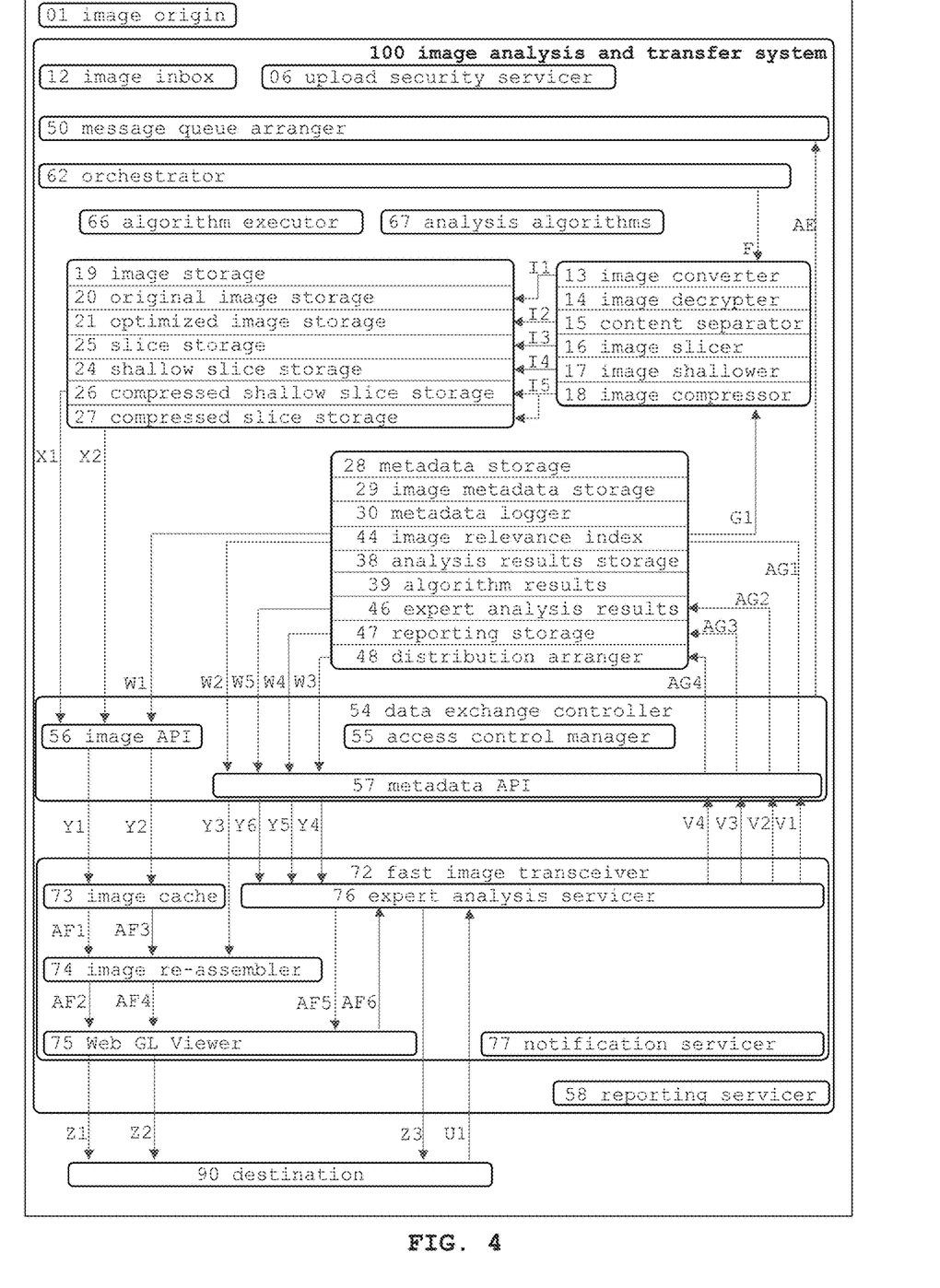
FIG. 4 shows schematics of the present system, depicting a simplified flow of transfer and expert (user) analysis of optimized image.

In the figures:
100 image transfer system
01 image origins
02 static image capturing device
03 mobile image capturing device
04 image filing system
06 image upload security servicer
07 image anonymizer
08 skull stripping algorithm
09 security relay
10 image encrypter
12 image Inbox
13 image converter
15 content separator
16 image slicer
17 image shallower
18 GZIP compressor
19 image storage
20 original image storage
21 optimized image storage
24 low precision slice storage
25 high precision slice storage
26 GZIP low precision slice storage
27 GZIP high precision slice storage
28 metadata storage
29 image metadata storage
30 processing logger
31 process logging metadata storage
32 transceiver data storage
33 image processing storage
34 image file import metadata storage
35 image transfer metadata storage
36 reporting metadata storage
37 image file export metadata storage
38 image analysis results storage
39 algorithms analysis results storage
40 contents analysis algorithm results storage
41 technical analysis algorithm results storage
42 contextual analysis algorithm results storage
43 synthesis algorithms result storage
44 image relevance metadata
45 including slice order relevance index
46 human expert analysis results storage
47 report storage
48 distribution arranger
50 message queue arranger
51 image queue arranger
52 algorithm input queue arranger
53 algorithm output queue arranger
54 data exchange controller
55 access control manager
56 image API
57 metadata API
58 reporting servicer
59 direct message reporter
60 email reporter 61 bulk image exporter
62 orchestrator
63 rule engine
64 virtual machine manager
65 transceiver controller
66 algorithm executor
67 analysis algorithms
68 contents analysis algorithms
69 technical analysis algorithms
70 context analysis algorithms
71 synthesis algorithms
72 fast image transceiver
73 image cache
74 image re-assembler
75 webgl viewer
76 expert analysis servicer
77 notification servicer
95 reporting queue arranger In all figures and given examples, schematics and description serve to the reader's understanding of the present system's functioning and logic, rather than to precisely represent the implementation. This particularly may go for the system's flow and how triggering and feedback is represented. Flow may be represented as direct flow from one component to another, or via storage (flow in rest). These types of flow may be interchangeable (e.g. FIG. 4 shows output from image converter 13 to reporting service 58 via image storage's 19 subcomponents. This may suggest that particular sequence is used, while rather a direct flow may be used from image converter 13 to reporting service 58, thereafter letting image storage's 19 subcomponents store the optimized image results. Regarding triggering, in some cases, triggering and feedback may be such a fundamental aspect of the present system, that it represented in the system's very structure (e.g. analysis algorithms 67 may only be triggered by algorithm executor 66, whereas output from algorithm executor 67 (including all algorithm analysis results) may only be regarded as feedback to orchestrator 62); and e.g. algorithm executor 66 may only be triggered by orchestrator 62, whereas output from algorithm executor 66 (including all algorithm analysis results, technical performance data) may only be regarded as feedback to orchestrator 62).

In the figures, triggers and flow may be represented by arrows.

For reasons of intelligibility, figures may only show components at a level relevant to the context of that particular figure. E.g. some figures show orchestrator 62 as such, i.e. without showing components orchestrator 62 comprises, whereas FIG. 3 shows orchestrator's 62 comprising components, even including message queue arranger's 50 comprising component, since they are essential for understanding in figure's 3 context.

Figure 1:
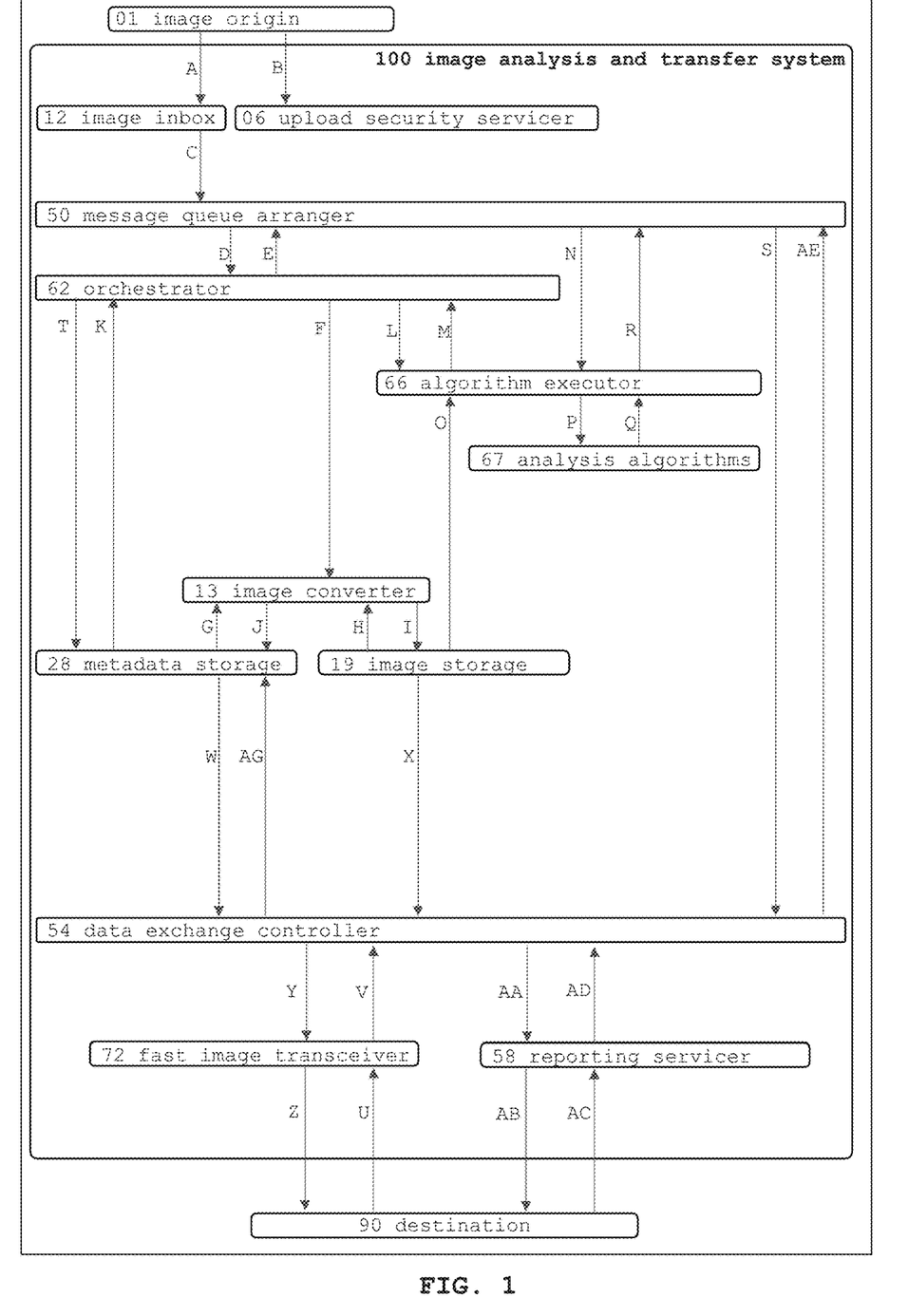
FIG. 1 shows schematics of the present system, depicting an overview.

Detailed description of FIG. 1: the present system's flow may be summarized as follows: complex digital images are uploaded and transferred in any format, with the purpose of 1) to quickly have a (graphical) version of the transferred image available at any location, 2) to quickly have analysis interpretation (metadata) available at any location, and 3) to quickly have both the graphical image and analysis interpretation available at any location.

Detailed description of FIG. 2: this figure shows schematics of the present system, depicting a simplified exemplary flow for secure upload, import and storage of an image file.

Detailed description of FIG. 3: this figure shows schematics of the present system, depicting an example of flow of analysis of an image file. Note that this flow has been highly simplified, since executing the analysis process may not be a predictable sequence of steps, but rather show very dynamic interaction instead, due to complexity caused by interdepending algorithms in combination with the necessity to enable guaranteed performance for critical use. The example aims to illustrate how analysis methods are determined and executed in a controlled manner. Analysis methods may be comprehensive. To ensure guaranteed availability of failsafe and timely execution for critical use, the present system is designed to process comprehensive analysis methods of relatively high complexity. A reason analysis methods may be comprehensive, is that a single image's analysis may require analysis of a multitude of images, which may be interrelated, each individual image may require a multitude of (types of) analysis algorithms, which may be interdepending, and for interrelated images as a whole, yet other algorithms or types of algorithms (e.g. synthesis algorithms) may be required. Managing such complexity may be partly an organisational concern, still analysis methods may be comprehensive. Some more reason for this are in the analysis method's purpose, e.g. analysis method for a brain image may require analysis of previously made brain images of the same person, e.g. representing different phases of the same stroke and/or past strokes. Other examples: e.g. analysis method of a single image may require analysis of images of other patients in similar cases (e.g. for reference, comparison, research), e.g. analysis method may concern different parts of the body; e.g. analysis method may comprise different types of images (e.g. CT and MR).

Yet other reasons analysis methods may be comprehensive, may be related to requirements for critical use, e.g. a relatively fine grained modular structure of algorithms may be beneficial for flexibility (e.g. enabling alternative analysis methods for fall-back) and scalability. Typically more than 500, such as more than 10000 modules may be present, having sizes of more than 10 code lines, such as up to 1000 code lines.

Image conversion is explained in more detail in FIG. 4 and the accompanying description and some other examples regarding fast image transfer via fast image transceiver 72.

Message queue arranger 50 may be able to autonomously process impact of priority change. Orchestrator 62 may trigger message queue arranger 50 to monitor for any conflicts in queue order, dependencies and/or hierarchy, to let rules engine 63 determine next steps. Some examples: e.g. checking for conflicting priorities/interdependencies, checking if sequences/dependencies may endanger time critical performance. Such sorts validation may include checking if suggested (e.g. highest) priority impact previously queued images (e.g. regarding timeliness). In case of any difficulties, rules engine 63 may determine what to do (e.g. suggest alternative analysis method and/or trigger reporting).

Time can be a trigger. Some examples: scheduled analysis may be triggered by the clock, e.g. when incoming image file transfers are announced or scheduled or e.g. for less critical use, such as for research purposes). In either case, rules engine 63 may trigger follow up after (rule based) decision-making upon method and priority of analysing the concerning image.

The present system may be capable of advance analysis, i.e. starting the analysis process in advance of receiving an image, so no image is available yet. For expected (announced) images to be uploaded, or during upload, orchestrator 62 may let rules engine 63 determine an analysis method, e.g. default for the expected type of file, or commonly used for images form a certain origin, etc. Rules engine 63 may need to make assumptions in this determination and will alter assigned analysis method if needed after the image is received. This may trigger virtual machine manager 64 to in advance allocate required technical resources. Advantages include that any time loss due to e.g. starting of virtual machine may be prevented. E.g. in early stages of the present system's development, starting virtual machines took up to 30% of throughput time of algorithm analysis. Please note that however the system is always on, some resources may be only used when needed. E.g. GPU usage may be expensive to have permanently available, while they may be unused a significant part of the time.

Rules engine 63 also may be triggered to initiate or alter the analysis process independent from any new image file arriving. Because the present system's complexity in combination with demanding requirements regarding availability, reliability and speed due to application for critical usage, rules engine 63 is "always awake". Reliability as well as speed can only be guaranteed thanks to the stacked setup of the system, in particular rules engine 63 continuously monitoring of all dynamics involved and rule based decision making upon these dynamics, leading to altered behaviour of the present system so that reliability can be ensured at any time. Some of these dynamics are e.g. controlled execution of interdepending analysis algorithms; e.g. during analysis an intermediate algorithms output may trigger a whole different analysis scenario, which may alter priority and/or destination; e.g. newly received image files may cause a changing priority of other images' analysis, unforeseen underperformance of analysis algorithms may urge orchestrator 62 to let virtual machine manager 64 dramatically scale up computing power; e.g. transceiver controller 65 may detect insufficient availability of virtual machines, which urges rules engine 63 to let both virtual machine manager 64 determine scale up and at the same time alter priorities of queued images files and/or queued algorithms; e.g. any or all of mentioned examples in combination with many more difficulties that may occur.

Rules engine 63 may trigger algorithm input queue arranger 52 to alter any algorithms in queue in accordance with alterations which rules engine 63 determines necessary due to any changed circumstances (e.g. higher priority is assigned to a newly received image).

Rules engine 63 may trigger image queue arranger 51 to alter file queues at any given moment, due to any dynamics, including environmental, leading to such a decision.

Rules engine 63 may trigger message queue arranger 50 to provide current and forecasted workload data from queues; message queue arranger 50 may trigger image queue arranger 51 to provide historic, current and forecasted workload data including numbers, types, status and priority of queued image files. Some examples of status are e.g. "currently being analysed", "waiting in queue, ready to be started", or e.g. "in queue, waiting for image file to be imported and registered" (in case of announced or scheduled images), or e.g. "analysis completed", etc.

Message queue arranger 50 may trigger algorithm input queue arranger 52 to provide historic, current and forecasted workload data including numbers, types, status and priority of queued algorithms (examples of status may be similar to above mentioned examples of image file queues' status) including queued algorithm inputs, which may include (intermediate) algorithm results as input for further analysis, such results may origin from different algorithms or from the same algorithm (e.g. phased outputs or intermediate results from algorithm "A" are stored by algorithm input queue arranger 52 as input for that very same algorithm "A" to continue, depending on results of interdepending algorithms "B", which is currently executed: e.g. algorithm "A" only may continue if algorithm "B" output matches a certain value, or e.g. continuation of algorithm "A" may be only valuable if output from a yet another algorithm "C" is available).

Message queue arranger 50 may trigger algorithm output queue arranger 53 to provide historic and current workload data including numbers, types, status and priority of queued algorithms and types of image files waiting in queue for execution, status may be waiting to be started or to be resumed which may be provided by image queue arranger 51 plus the requires analysis algorithms to be executed for these image files, provided by algorithms queues input arranger 52.

This concerns both files i.e. for which analysis execution yet has to be started or resumed, provided by image queue arranger 51; e.g. analysis algorithms waiting in queue to be started or resumed.

Message queue arranger 50 may trigger rules engine 63 providing information about currently executed and scheduled/upcoming activity, to provide "insight" in work currently executed (e.g. number and types of images currently analysed and algorithms currently running) and to enable rules engine 63 in forecasting. Rules engine 63 needs this information as input for its continuous decision making, in combination with other inputs, which may include performance monitoring data as provided by transceiver controller 65.

Transceiver controller 65 may trigger rules engine 63, providing all data regarding the present system's workload and performance rules engine 63 needs to calculate and steer performant execution. Transceiver controller 65 may provide current and historic data as well as forecasted data of this kind.

Detailed description of FIG. 4: this figure shows schematics of the present system, depicting a simplified flow of fast image transfer, using fast image transceiver 72 to re-assemble optimized image data for expert analysis.

Some more details: an image may be completely or partially be downloaded in low precision slices. After render, in the background, the high precision complement downloaded, and merged with its low precision slice equivalent. This allows for decreased click to render times up to 4 times (16 bit instead of 64 bit). In many cases, user 90 may not notice the image is not completely available in high resolution. User's 90 interaction with the fast image transceiver may be slower than the completion of the image in the background—e.g. the available low precision parts available may be sufficient for a for a first glance; before user 90 starts browsing and windowing, the relevant parts involved may be completed in high resolution in the background.

Images received in a medical image file format may be unsuitable for web use. Conversion into 2D slices may be stored as byte arrays suitable for web use. Image API 56 serves 3D image as separate 2D slices, this allows for faster initial display (render on first available slice), this allows for changing slice display order (most relevant first), this allows for selective slice caching in image cache 73; image slices may be stored as lossless Compressed GZIP. Modern browsers can automatically decompress gzip data using highly optimized code. Downloaded image slices may be cached by image cache 73 in browser and kept between sessions. On cache limit, cache may be purged based on a number of factors, e.g. slice relevance within image, low precision preference, patient scan date. Rendering of image slices may be done using web GL viewer 75, which allows for device GPU acceleration.

Any next steps (not depicted in FIG. 4) following image transfer and/or user analysis may be triggered by orchestrator 62, which may continuously monitor metadata storage 28, letting rule engine 63 determine and assign next steps (e.g. reporting, e.g. forwarding a transferred image to a different user, following instructions provided by user 90 using expert analysis servicer 76), triggering message queue arranger 50 to store these next steps for further processing.

Note that fast image transceiver 72 may trigger user 90 (not depicted in FIG. 4) by letting notification servicer 77 alert user 90 (e.g. about an upcoming image transfer, e.g. about a status update regarding a forwarded image transfer). This may practical in case a user actively uses fast image transceiver 72, e.g. implemented as a mobile app, and/or e.g. user is already/still logged in the web application. Alerting may also occur using the present system's reporting servicer 58.

The preceding examples can be repeated with similar success by substituting the generically or specifically described components and/or operating conditions of embodiments of the present invention for those used in the preceding examples.

Optionally, embodiments of the present invention can include a general or specific purpose computer or distributed system programmed with computer software implementing steps described above, which computer software may be in any appropriate computer language, including but not limited to C++, FORTRAN, BASIC, Java, Python, Linux, assembly language, microcode, distributed programming languages, etc. The apparatus may also include a plurality of such computers/distributed systems (e.g., connected over the Internet and/or one or more intranets) in a variety of hardware implementations. For example, data processing can be performed by an appropriately programmed microprocessor, computing cloud, Application Specific Integrated Circuit (ASIC), Field Programmable Gate Array (FPGA), or the like, in conjunction with appropriate memory, network, and bus elements. One or more processors and/or microcontrollers can operate via instructions of the computer code and the software is preferably stored on one or more tangible non-transitive memory-storage devices.

Embodiments of the present invention provide a technology-based solution that overcomes existing problems with the current state of the art in a technical way to satisfy an existing problem in the realm of computer processing of digital images, particularly for those working in fields (such as emergency medicine) that depends on urgent processing and transfer of digital images. An embodiment of the present invention is necessarily rooted in computer technology in order to overcome a problem specifically arising in the realm of computers. Embodiments of the present invention achieve important benefits over the current state of the art, such as faster transfer times, smaller memory requirements, and more efficient use of processing capabilities.

Note that in the specification and claims, "about" or "approximately" means within twenty percent (20%) of the numerical amount cited. All computer software disclosed herein may be embodied on any non-transitory computer-readable medium (including combinations of mediums), including without limitation CD-ROMs, DVD-ROMs, hard drives (local or network storage device), USB keys, other removable drives, ROM, and firmware.

Embodiments of the present invention can include every combination of features that are disclosed herein independently from each other. Although the invention has been described in detail with particular reference to the disclosed embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference. Unless specifically stated as being "essential" above, none of the various components or the interrelationship thereof are essential to the operation of the invention. Rather, desirable results can be achieved by substituting various components and/or reconfiguration of their relationships with one another.

The invention claimed is:

1. A modular digital image transfer system comprising:
an input for receiving a plurality of digitized images,
an output for transferring at least one digitized and processed image to a receiving device, and
a dedicated system for processing comprising a multitude of parallel and/or serial operable processors, wherein at least>10 parallel operable processors are present, the dedicated system comprising
an image inbox for digital images,
an orchestrator orchestrating its modular structure and computing power comprising a rule engine, a virtual machine manager for managing the multitude of parallel and/or serial operable processors, a transceiver controller for performance monitoring, a queue arranger driver, an algorithm executor driver, an input in use receiving images from a message queue arranger, an output in use providing images to a reporting servicer, and an output in use providing instructions to an algorithm executor,
the message queue arranger for determining queued files priority and to register assigned analysis algorithms in queue comprising an input in use receiving images from the image inbox, an input in use receiving image analysis results from the algorithm executor, an output in use providing instructions to the algorithm executor, an output in use providing images to the reporting servicer, and an output in use providing images to the orchestrator,
the algorithm executor comprising image analysis algorithms, wherein the image analysis algorithms comprise at least two layers in use analysing the image, an input in use receiving images from the message queue arranger, an input in use receiving images from an image storage, an input in use receiving metadata from a metadata storage, an input in use receiving instructions from the orchestrator, an output in use providing processed images to the reporting servicer, and an output in use providing feedback to the message queue arranger,
a data exchanger, comprising an input in use receiving instructions from a user, an output in use providing processed images to the reporting servicer, and an output in use providing unprocessed images to the reporting servicer, the reporting servicer comprising
an input in use receiving processed images from the algorithm executor,
an input in use receiving instructions from the algorithm executor,
an input in use receiving images from a data exchange controller, and
an output in use providing reports to the data exchange controller or user, a fast image transceiver in use receiving input from the data exchange controller and providing output to the orchestrator, the metadata storage, and the image storage.

2. The modular digital image transfer system according to claim 1, wherein the data exchange controller comprises at least one of an access control manager, an image API, and a metadata API.

3. The modular digital image transfer system according to claim 1, wherein the message queue arranger comprises at least one of an image file queue arranger, an algorithm input queue arranger, and an algorithm output queue arranger.

4. The modular digital image transfer system according to claim 1, wherein the reporting servicer comprises at least one of a direct message reporter, and an email reporter.

5. The modular digital image transfer system according to claim 1, wherein the metadata storage comprises an input in use receiving instructions from the orchestrator, an input in use receiving instructions from the data exchange controller, and an output in use providing data to the reporting servicer.

6. The modular digital image transfer system according to claim 1, comprising an image converter receiving the plurality of digitized images for dividing parts of an image and transferring said parts to the multitude of parallel and/or serial operable processors of the dedicated system.

7. The modular digital image transfer system according to claim 1, comprising an image re-assembler for reassembling processed parts of the dedicated system.

8. The modular digital image transfer system according to claim 1, wherein each of the parallel and/or serial operable processors has a response time of<20 sec, and/or
wherein each of the parallel and/or serial operable processors has an uptime of>99.5%, and/or
wherein each of the parallel and/or serial operable processors has a mean time between failure (MTBF) of>10 days.

9. The modular digital image transfer system according to claim 1, wherein the image is selected from the group consisting of: a CT scan, an MRI scan, and a PET scan.

10. The modular digital image transfer system according to claim 1, wherein each available processor is labelled with a success rate chance label, and/or wherein in use sub-image parts are identified and labelled by the algorithm executor.

11. The modular digital image transfer system according to claim 1, comprising a trigger for starting an information loop, and/or an image slicer capable of converting 3D-images into 2D-sliced images, and/or a GZIP compressor, wherein in use the GZIP compressor transfers a low precision slice and high precision slice in GZIP compressed format, and/or an image cache which in used is capable of decompressing, and/or an image shallower wherein in use converting an image into a low precision slice, and/or an image converter capable of converting an image into a byte array format, a metadata API, an image API, the image converter having an input capable of receiving images, and an output capable of transferring converted images to the metadata API and to the image API, the metadata API having an input capable of receiving metadata from the converter and an output capable of transferring metadata to the slice arranger, the image API having an input capable of receiving image data from the converter and an output capable of transferring image data to an image re-assembler for reassembling processed parts of the dedicated system.

12. A method of operating the modular digital image transfer system according to claim 1, comprising:
receiving a plurality of images in the image inbox,
arranging the plurality of images by the message queue arranger,
processing a first image on instruction of the orchestrator by the algorithm executor,
reporting the processed image by the reporting servicer,
transferring the processed image by the fast image transceiver, and repeating processing and reporting for subsequent images.

13. A computer program for digital image transfer comprising instructions loaded on at least one computer for carrying out the following steps:
providing the modular digital image transfer system according to claim 1,
receiving at least 10 digital medical images,
providing modules for processing and transferring images, each module forming a part of the modular digital image transfer system,
dividing images into sub-images,
parallel processing of both the sub-images and modules,
creating metadata,
controlling and optimizing parallel processing, modularity, image processing, and relevance,
transferring the sub-images, and
recombining the sub-images at least partially.

* * * * *